US008546137B2

(12) United States Patent
Cannon et al.

(10) Patent No.: US 8,546,137 B2
(45) Date of Patent: Oct. 1, 2013

(54) INHIBITION OF DENDRITIC CELL-DRIVEN REGULATORY T CELL ACTIVATION AND POTENTIATION OF TUMOR ANTIGEN-SPECIFIC T CELL RESPONSES BY INTERLEUKIN-15 AND MAP KINASE INHIBITOR

(75) Inventors: Martin J. Cannon, Little Rock, AR (US); Kellie L. Kozak, Galveston, TX (US); Timothy J. O'Brien, Little Rock, AR (US)

(73) Assignees: The Board of Trustees of the University of Arkansas, Little Rock, AR (US); National Institutes of Health, US Dept. of Health and Human Services, Bethesda, MD (US)

( * ) Notice: Subject to any disclaimer, the term of this patent is extended or adjusted under 35 U.S.C. 154(b) by 259 days.

(21) Appl. No.: 12/286,122

(22) Filed: Sep. 27, 2008

(65) Prior Publication Data

US 2009/0136447 A1 May 28, 2009

Related U.S. Application Data

(60) Provisional application No. 60/995,738, filed on Sep. 27, 2007.

(51) Int. Cl.

| | |
|---|---|
| ***C12N 5/071*** | (2010.01) |
| ***C12N 5/00*** | (2006.01) |
| ***C12N 5/02*** | (2006.01) |

(52) U.S. Cl.
USPC ......... 435/372; 435/372.3; 435/377; 435/373

(58) Field of Classification Search
None
See application file for complete search history.

(56) References Cited

U.S. PATENT DOCUMENTS

| | | | | |
|---|---|---|---|---|
| 6,746,670 | B2 | 6/2004 | Levings | |
| 2004/0022761 | A1 * | 2/2004 | Banchereau et al. | 424/85.2 |

OTHER PUBLICATIONS

Xie et al., 2005. Exp. Hem. vol. 33: 564-572.*
EMD product information, 2011, pp. 1-2.*
Kretschmer et al., 2005, Nat. Immunol. vol. 6: 1219-1227.*
Nakahara et al., 2006, J. Derm. Sci. vol. 42: 1-11.*
Wang et al. Published online, Nov. 2005, Blood, vol. 107: 2432-2439.*
Duraisingham et al., 2010, Immunology, 131: 210-219.*
Woltman et al., 2003, J. Leuk. Biol. vol. 73: 428-441.*

* cited by examiner

*Primary Examiner* — Amy Juedes
(74) *Attorney, Agent, or Firm* — Hugh McTavish

(57) ABSTRACT

The invention involves the discovery that if dendritic cells loaded with a tumor antigen are cultured in interleukin-15 (IL-15), or if T cells activated by the dendritic cells are cultured in IL-15, Treg activity that is specific for the tumor antigen is reduced. This reduction in Treg activity results in an increase in anti-tumor immune response. Another embodiment of the invention involves the discovery that incubating dendritic cells with a MAP kinase inhibitor in combination with IL-15 gives synergistic benefits when the dendritic cells are used to activate T cells. Dendritic cell and T cell compositions incubated with IL-15 or a MAP kinase inhibitor are provided.

6 Claims, 8 Drawing Sheets

Non-irradiated peptide-specific CD4$^{+}$ T cells

Irradiated peptide-specific CD4$^{+}$ T cells

Non-irradiated peptide-specific CD8$^{+}$ T cells

INHIBITION OF DENDRITIC CELL-DRIVEN REGULATORY T CELL ACTIVATION AND POTENTIATION OF TUMOR ANTIGEN-SPECIFIC T CELL RESPONSES BY INTERLEUKIN-15 AND MAP KINASE INHIBITOR

This application claims benefit of priority under 35 U.S.C. 119(e) of U.S. provisional patent application No. 60/995,738, filed Sep. 27, 2007.

STATEMENT REGARDING FEDERALLY SPONSORED RESEARCH

Development of this invention was supported by a grant from the United States National Institutes of Health. The United States government may have certain rights in this invention.

BACKGROUND

While identification of tumor-specific target antigens has been a major hurdle to overcome for prevention of cancer progression by vaccination or immunotherapy, a second challenge has been the induction of immune responses to these "self" antigens. Tumor antigen-specific primary T cell responses must be induced from naïve T cells in the peripheral blood, or alternatively from primed, but anergic or tolerized T cells. The prospects for immunological treatment of cancer have risen sharply in recent years, based in part on the identification of dendritic cells (DC) as powerful professional antigen-presenting cells capable of inducing primary $CD4^+$ helper T cell and $CD8^+$ cytotoxic T lymphocyte (CTL) responses in vitro and in vivo. Clinical trials of DC vaccination have demonstrated induction of anti-tumor immune responses, and therapeutic benefit has been observed in a proportion of patients, but responses are inconsistent and it is clear that current approaches are not optimal (1).

In addition to the technical challenges of vaccination with ex vivo-generated DC, there is a burgeoning appreciation that tumor-associated $CD4^+$ regulatory T cells (Treg) represent a major barrier to effective DC vaccination and other forms of active or passive cellular immunotherapy (2-4). The clinical significance of tumor-associated $CD4^+$ Treg was highlighted by the work of Curiel and colleagues, who showed that Treg are recruited to ovarian tumors by the chemokine CCL22 (predominantly expressed by ovarian tumors), and that the presence of Treg confers immune privilege and is associated with a poor prognosis and increased mortality (5). These observations are underlined by further studies showing that high expression of the forkhead box transcription factor P3 (Foxp3), which is preferentially expressed by $CD4^+$ Treg, is an independent prognostic factor for reduced overall survival in ovarian cancer (6). Such findings lend credence to the notion that strategies for depletion of tumor-associated Treg, or inhibition of Treg function, may be of therapeutic benefit, particularly in conjunction with active, tumor-specific immunotherapy. Indeed, a recent clinical trial of tumor RNA-transfected DC vaccination combined with denileukin diftitox (a fusion protein of IL-2 and diphtheria toxin, which targets CD25 preferentially expressed by $CD4^+$ Treg) for patients with renal cell carcinoma resulted in reduced numbers of Treg in the peripheral blood and enhanced generation of tumor-specific T cell responses (7).

While there is an increasing consensus that active immunotherapy or antitumor vaccination should be supported by selective and efficient depletion of Treg, there is also a new appreciation that vaccination itself may induce or expand Treg, thus promoting tumor-specific tolerance. Vaccination with recombinant vaccinia virus in a mouse tumor model system resulted in expansion of both effector and regulatory T cells, with Treg function being dominant, blocking effector function in vitro and in vivo (8). In a notable clinical study, injection of DC matured with inflammatory cytokines (TNFα, IL-1β, IL-6 and $PGE_2$) expanded $foxp3^+CD4^+$ Treg in 3 of 3 myeloma patients tested (9). While it is well known that immature DC induce Treg and peripheral tolerance (10-12), the finding that mature DC can also expand Treg has come as an unpleasant surprise, and has serious implications for current approaches to DC vaccination. From these observations, it is apparent that although depletion of Treg prior to vaccination may be necessary, Treg depletion alone will not be sufficient for optimal post-vaccine effector function and antitumor immunity. Redirection of DC-driven maturation and function will also be required to prevent de novo induction of vaccine antigen-specific Treg.

Improved treatments for cancer are needed, including improved methods of vaccinating to induce a patient's own immune system to attack his cancer. Improved methods of vaccinating to prevent cancer are also needed. Improved vaccination methods to treat or prevent other diseases are also needed.

SUMMARY

One embodiment of invention is based on the discovery that interleukin-15 (IL-15) antagonizes or down-regulates the activity of regulatory T cells (Treg cells). Treg cells down-regulate the activity of other immune cells. This is needed especially to prevent immune response against healthy self tissue. An excessive immune response against self tissue is responsible for autoimmune diseases, such as type I diabetes and rheumatoid arthritis. So in the context of preventing autoimmune disease, activity of Treg cells is beneficial. But in the context of anti-cancer therapy Treg activity may be deleterious. A promising anti-cancer strategy is to vaccinate a cancer patient with antigens from their own tumor to try to induce an immune response against the tumor. In this context, if the vaccine activates Treg cells, the activated Treg cells may promote tumor-specific tolerance and block effective antitumor immunity.

The inventors have contacted tumor-antigen-loaded dendritic cells with responder T cells to induce a T cell immune response that kills tumor cells. They have found that if either or both of the dendritic cells or T cells are cultured in IL-15, Treg activity that is specific for the tumor antigen is reduced. This reduction in Treg activity results in an increase in antitumor immune response. The specific antigens used for these experiments were from matriptase, an antigenic protein linked to ovarian cancer.

In addition, the inventors have found that if the dendritic cells are cultured in a mitogen-activated protein (MAP) kinase inhibitor, specifically a p38 MAP kinase inhibitor, three beneficial effects are achieved for reducing Treg activity and increasing T cell activity against tumors in vivo. Treatment of dendritic cells (DC) with IL-15 in combination with a p38 MAP kinase inhibitor markedly inhibited generation of Foxp3-positive CD4+ regulatory T cells and markedly potentiated CD4+ helper T cell cytokine expression upon stimulation with tumor antigen. Treatment of DC with the combination of IL-15 and the p38 MAP kinase inhibitor also increased CD4+ expression of CCR4, a receptor for the CCL22 chemokine that is responsible for trafficking of T cells into the tumor microenvironment. Thus, this is expected to increase T cell trafficking into tumors. Finally, treatment of DC with IL-15 and/or a p38 MAP kinase inhibitor diminishes CD4+ T cell expression of the inhibitory receptor PD-1. The ligand for PD-1 is B7-H1, which is widely expressed in human tumors and is responsible for induction of programmed cell death (apoptosis) of anti-tumor effector T cells. Diminished expression of PD-1 is thus expected to confer a survival advantage on tumor-infiltrating effector T cells.

Thus, one aspect of the invention involves a method of reducing Treg antigen-specific activity in response to a vaccine (especially a cancer vaccine) involving culturing dendritic cells loaded with an antigen in the presence of IL-15, and then administering the antigen-loaded dendritic cells as a vaccine. Another aspect of the invention involves a method of reducing Treg antigen-specific activity in response to a vaccine involving administering the vaccine in conjunction with administering IL-15.

Importantly, the inventors showed that the effects of maturing dendritic cells (DC) in the presence of IL-15 and then contacting the dendritic cells with T cells also in the presence of IL-15 to stimulate the T cells were synergistic. That is, treatment of DC with IL-15 or treatment of CD4+ T cells with IL-15 each resulted in a small increase in the frequency of T cells expressing TNFα or IFNα (two cytokines indicative of activated T cells), but combined IL-15 treatment of both DC and CD4+ T cells resulted in a synergistic gain in antigen-driven cytokine response.

Likewise, IL-15 and a p38 MAP kinase inhibitor used together to culture DC synergistically reduced Foxp3 cell-surface expression in DC-activated CD4+ T cells, synergistically increased TNF-alpha cytokine expression in DC-activated CD4+ T cells, and synergistically increased CCR4 expression in DC-activated CD4+ T cells.

One embodiment of the invention provides a therapeutic composition comprising: (1) antigen-specific T cells cultured ex vivo in IL-15 in an amount and for a time effective to reduce Treg activity of the antigen-specific T cells; or (2) antigen-specific T cells stimulated ex vivo with dendritic cells that are cultured ex vivo in IL-15 in an amount and for a time effective to reduce Treg activity of the antigen-specific T cells; or (3) dendritic cells loaded with an antigen and cultured ex vivo in a combination of IL-15 and a MAP kinase inhibitor in amounts and for a time effective to reduce Treg activity specific for the antigen in T cells contacted with the dendritic cells and to reduce Foxp3 expression in T cells contacted with the dendritic cells.

Another embodiment of the invention provides a method of preparing a therapeutic composition comprising antigen-specific T cells or dendritic cells loaded with an antigen, the method comprising: (1) culturing antigen-specific T cells ex vivo in IL-15 in an amount and for a time effective to reduce Treg activity of the antigen-specific T cells; or (2) stimulating antigen-specific T cells ex vivo with antigen-loaded dendritic cells that are cultured ex vivo in IL-15 in an amount and for a time effective to reduce Treg activity of the antigen-specific T cells; or (3) culturing antigen-loaded dendritic cells ex vivo in a combination of IL-15 and a MAP kinase inhibitor in amounts and for a time effective to reduce Treg activity specific for the antigen in T cells contacted with the dendritic cells and to reduce Foxp3 expression in T cells contacted with the dendritic cells.

Another embodiment provides a method of reducing Treg activity of T cells comprising: (a) stimulating T cells ex vivo with antigen-loaded dendritic cells that are cultured ex vivo in IL-15 in an amount and for a time effective to reduce Treg activity of the T cells specific for the antigen; and/or (b) culturing antigen-specific T cells ex vivo in IL-15 in an amount and for a time effective to reduce Treg activity of the antigen-specific T cells.

Another embodiment of the invention provides a dendritic cell composition comprising: dendritic cells loaded with an antigen and cultured ex vivo in a combination of IL-15 and a MAP kinase inhibitor in amounts and for a time effective to reduce Treg activity specific for the antigen in T cells contacted with the dendritic cells and to reduce Foxp3 in T cells contacted with the dendritic cells.

One embodiment of the invention provides a method of inhibiting Treg activity in response to a vaccine, the method comprising: administering IL-15 to a human patient sequentially or concurrently with a vaccine containing an antigen to induce an immune response in the human patient to the antigen; wherein the IL-15 is administered in an amount effective to inhibit Treg activity specific for the antigen.

Another embodiment of the invention provides a method of administering a dendritic cell vaccine comprising: (a) administering to a patient a vaccine comprising dendritic cells loaded with an antigen; and (b) concurrently or sequentially with administering the vaccine, administering to the patient an amount of interleukin-15 effective to reduce Treg responses in the patient specific to the antigen; wherein the dendritic cells are cultured ex vivo in IL-15 in an amount and for a time effective to reduce Treg responses in the patient specific to the antigen.

Another embodiment of the invention provides a dendritic cell vaccine comprising: (a) dendritic cells loaded with an antigen and cultured ex vivo in IL-15 in an amount and for a time effective to reduce Treg activity specific for the antigen in T cells contacted with the dendritic cells; and (b) interleukin-15 in an amount effective to reduce Treg activity specific for the antigen.

Another embodiment of the invention provides a method of preparing dendritic cells for a vaccine to reduce regulatory T cell activation, the method comprising: (a) culturing antigen-loaded dendritic cells ex vivo in IL-15 in an amount and for a time effective to reduce Treg responses in a human patient specific to the antigen; and (b) incorporating the dendritic cells into a vaccine for administration to a human patient.

DETAILED DESCRIPTION

Definitions

Figure 3:
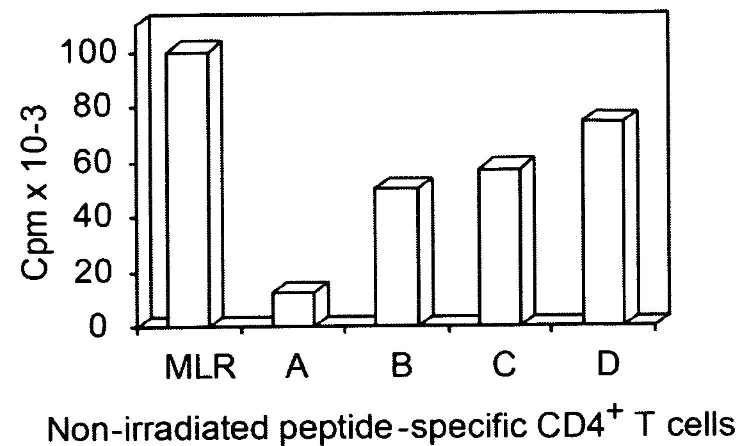
FIG. 3. IL-15 antagonism of Treg function. Matriptase 170-204 peptide-specific $CD4^+$ or $CD8^+$ T cells activated with conventional or IL-15 treated DC and maintained with IL-2 or IL-2 plus IL-15 were tested for Treg activity in 3 day cocultures with autologous alloreactive $CD4^+$ T cells at a 1:1 ratio. Alloreactive $CD4^+$ T cells were stimulated with allogeneic irradiated LCL. $^3$H-TdR was added for the final 16 hours of culture. Results are presented as the mean counts of 4 replicate cultures of alloreactive $CD4^+$ T cells in the one-way MLR alone, or in coculture with DC-activated peptide-specific T cells. For the results presented in the middle panel, the peptide-specific $CD4^+$ T cells were irradiated (2,500 cGy) before coculture. Peptide-specific $CD4^+$ or $CD8^+$ T cells were activated with conventional DC and maintained with IL-2 (A), activated with IL-15-treated DC and maintained with IL-2 (B), activated with conventional DC and maintained with IL-2 plus IL-15 (C), or activated with IL-15 treated DC and maintained with IL-2 plus IL-15 (D).
Figure 3:
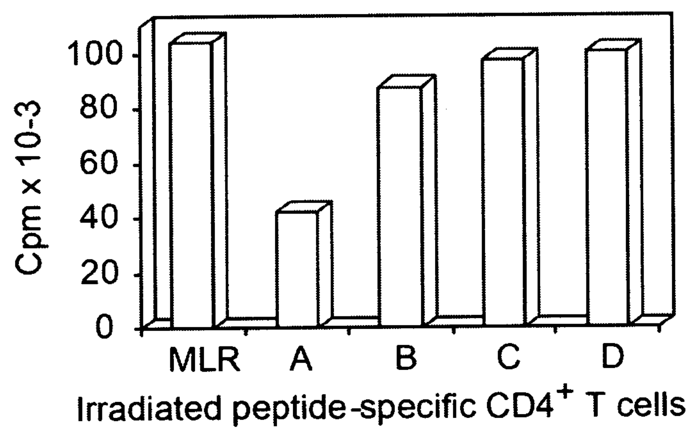
Figure 3:
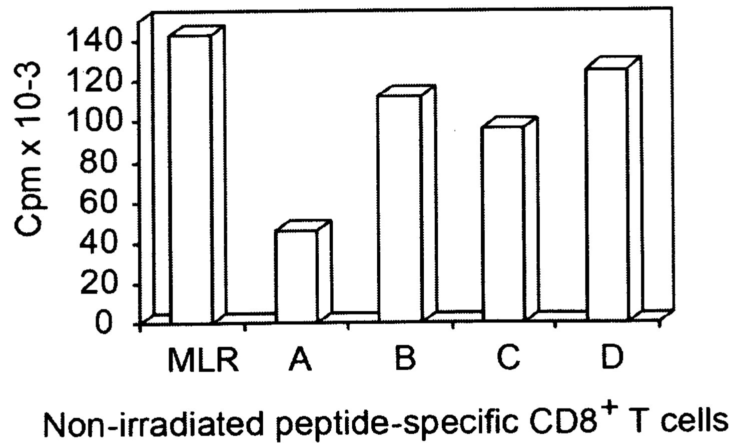

CD4+ and CD8+ Treg activity can be assayed as described in the experiments of Example 1 below whose results are shown in FIG. 3. "Inhibiting CD4+ or CD8+ Treg activity specific for an antigen" is shown by inhibiting the ability of antigen-specific CD4+ or CD8+ cells to reduce proliferation of alloreactive CD4+ cells in response to allogeneic irradiated lymphoblastoid cell lines (LCL), as shown in Example 1 with the experiments whose results are shown in FIG. 3. Inhibition of Treg activity is inhibition as compared to T cells cultured conventionally (i.e., without IL-15) with stimulation of dendritic cells cultured conventionally (i.e., without IL-15 and without a MAP kinase inhibitor).

Figure 6:
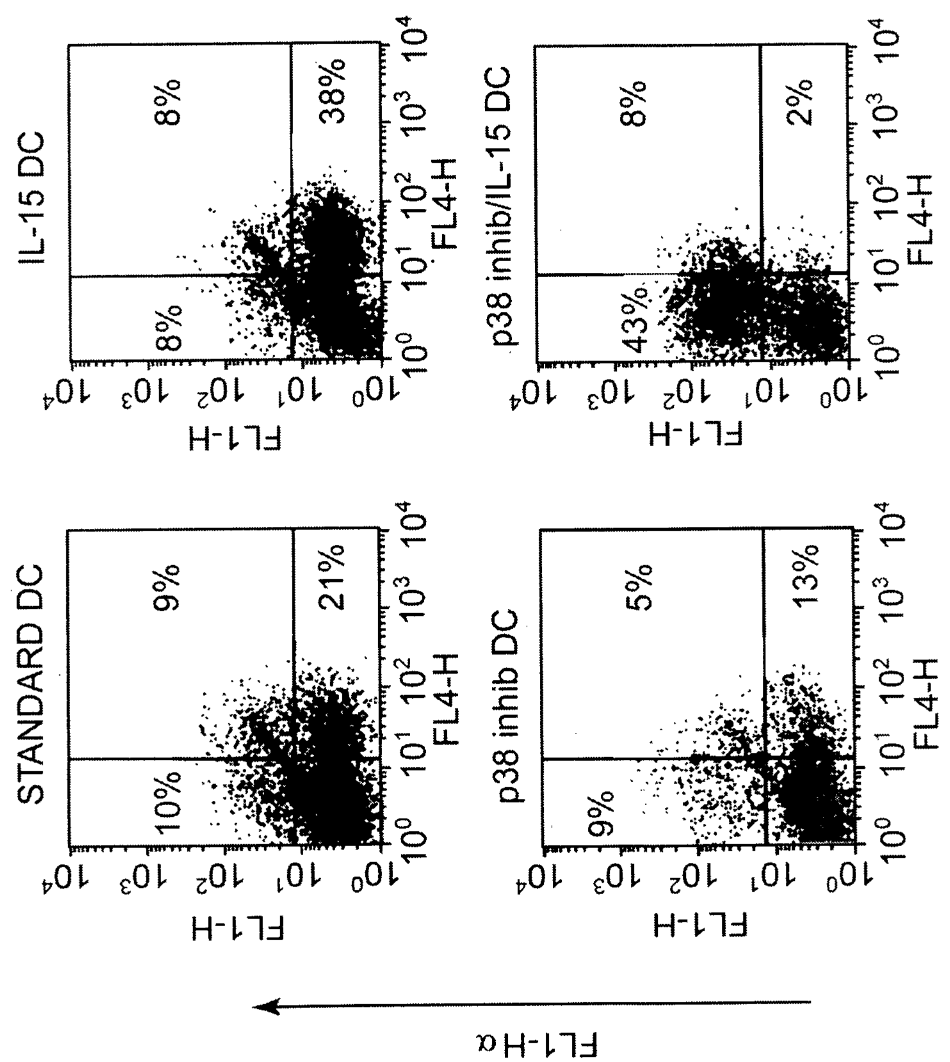
FIG. 6. TNFα and Foxp3 expression by tumor antigen-specific CD4+ T cells stimulated with DC treated IL-15 and/or p38 MAP kinase inhibitor. Tumor antigen peptide-specific $CD4^+$ T cells were activated with hepsin 48-84 peptide-loaded conventional DC, IL-15-treated DC, DC treated with a p38 MAP Kinase inhibitor, or DC treated with both IL-15 and a p38 MAP kinase inhibitor. All $CD4^+$ T cell cultures were maintained with IL-2.

Foxp3 expression is assayed as described in the Experiments of Example 2 below whose results are shown in FIG. 6. "Reduction of Foxp3 expression" refers to reduction as compared to expression in T cells cultured conventionally (i.e., without IL-15) with stimulation of dendritic cells cultured conventionally (i.e., without IL-15 and without a MAP kinase inhibitor).

Description

The inventors have found that if T cells are activated with dendritic cells loaded with matriptase antigenic peptide, these T cells down-regulate the proliferative response of autologous alloreactive T cells stimulated by allogeneic lymphoblastoid cell line cells (LCL). That down-regulation is regulatory T cell activity. If the dendritic cells are cultured in IL-15, the Treg activity is reduced. If the peptide-specific T cells are cultured in IL-15, their Treg activity is reduced. If both IL-15-matured DC and IL-15 in the culture of the peptide-specific T cells are used, the effects of reducing Treg activity are greater still.

Likewise, activation with IL-15-matured dendritic cells and culture in IL-15 have an additive effect in stimulating peptide-specific cytotoxic activity of both CD4+ and CD8+ cells against peptide-loaded autologous LCL.

The use of IL-15-matured dendritic cells to activate peptide-specific CD4+ cells and culture of the peptide-specific CD4+ cells in IL-15 both modestly increased antigen-specific CD4+ Th1 cytokine expression, but together they had a much larger synergistic effect in stimulating Th1 cytokine expression upon challenge with peptide-loaded autologous LCL.

It has also been found that culturing dendritic cells in a MAP kinase inhibitor, preferably a p38 MAP kinase inhibitor, has beneficial effects on the activity of T cells stimulated with the dendritic cells loaded with antigen. Specifically, IL-15 and a p38 MAP kinase inhibitor used together to culture DC synergistically reduced Foxp3 expression in CD4+ T cells activated with the DC, syngergistically increased TNF-alpha cytokine expression in DC-activated CD4+ T cells, and synergistically increased CCR4 expression in DC-activated CD4+ T cells.

Forkhead box transcription factor P3 (Foxp3) is considered a marker of Treg cells. Increased Foxp3 expression may be indicative of the number of Treg cells. Thus, decreasing Foxp3 expression should correlate with the number of Treg cells and therefore Treg activity.

TNF-alpha cytokine expression is indicative of activated T cells, so increasing TNF-alpha levels indicates improved tumor antigen-specific activation of cytotoxic CD4+ and CD8+ T cells. Increased TNF-alpha levels also indicates a Th1 cytokine profile, which is regarded as advantageous for cancer vaccines or immunotherapy.

CCR4 and CXCR4 are both cell surface markers that bind to CCL22 and CXCL12, respectively (42, 43), both of which are abundantly produced in epithelial cancers, including ovarian tumors (42, 44). Increasing expression of CCR4 and CXCR4 is expected to promote trafficking of the antigen-specific T cells into the tumor microenvironment, thus improving their targeting and activity against tumors.

One embodiment of the invention provides a therapeutic composition comprising: (1) antigen-specific T cells cultured ex vivo in IL-15 in an amount and for a time effective to reduce Treg activity of the antigen-specific T cells; or (2) antigen-specific T cells stimulated ex vivo with dendritic cells that are cultured ex vivo in IL-15 in an amount and for a time effective to reduce Treg activity of the antigen-specific T cells; or (3) dendritic cells loaded with an antigen and cultured ex vivo in a combination of IL-15 and a MAP kinase inhibitor in amounts and for a time effective to reduce Treg activity specific for the antigen in T cells contacted with the dendritic cells and to reduce Foxp3 expression in T cells contacted with the dendritic cells. The therapeutic composition is suitable for injection into a human or other mammal. It typically includes a pharmaceutically acceptable diluent and is free of bacteria and other pathogens.

In one embodiment, the therapeutic composition comprises antigen-specific T cells stimulated ex vivo with dendritic cells that are cultured ex vivo in IL-15 in an amount and for a time effective to reduce Treg activity of the antigen-specific T cells; wherein in addition the antigen-specific T cells are cultured ex vivo in IL-15 in an amount and for a time effective to reduce Treg activity of the antigen-specific T cells.

Preferably, where it is stated that dendritic cells or T cells are cuultured in IL-15 or a combination of IL-15 and a MAP kinase inhibitor at concentrations and for a time effective to reduce Treg activity of antigen-specific T cells, the antigen-specific T cells inhibit alloreactive CD4+ T cell proliferation, as assayed in the experiments whose data are shown in FIG. 3 herein, by less than 70%, more preferably by less than 60%. The experiments whose results are shown in FIG. 3 are discussed more fully in Example 1 below. But briefly, in FIG. 3, top panel, proliferation of non-iradiated peptide-specific DC4+ T cells in the mixed lympocyte reaction is inhibited by about 90% by the addition T cells activated conventionally (without IL-15) with antigen-loaded conventionally prepared DC (DC cultured without IL-15 or a MAP kinase inhibitor) (comparing bar A to bar MLR). This reflects Treg activity of the antigen-specific T cells. In contrast, T cells cultured with IL-15, or T cells activated by DC cultured with IL-15, or T cells cultured in IL-15 and activated by DC cultured in IL-15 each inhibited the mixed lymphocyte reaction by less than 60% (bars B, C, and D compared to bar MLR in the top panel of FIG. 3).

In one embodiment of the therapeutic composition, the therapeutic composition comprises: (i) dendritic cells loaded with an antigen and cultured ex vivo in a combination of IL-15 and a MAP kinase inhibitor in amounts and for a time effective to reduce Treg activity specific for the antigen in T cells contacted with the dendritic cells and to reduce Foxp3 expression in T cells contacted with the dendritic cells; and (ii) IL-15 in an amount effective to reduce Treg activity specific for the antigen.

In specific embodiments of the compositions of the invention the dendritic cells of part (3) are loaded with an antigen and cultured ex vivo in a combination of IL-15 and a MAP kinase inhibitor in amounts and for a time effective to reduce Treg activity specific for the antigen in T cells contacted with the dendritic cells and to reduce Foxp3 expression in T cells contacted with the dendritic cells.

Preferably, where Foxp3 expression is disclosed to be reduced herein, it is reduced at least 2-fold.

A variety of MAP kinase inhibitors are available from several commercial sources, including Calbiochem (EMD Chemicals, Inc., 480 S. Democrat Road, Gibbstown, N.J. 08027, USA). Examples of MAP kinase inhibitors include PD98059 (2'-amino-3'-methoxyflavone), SB202190 (4-(4-fluoophenyl)-2-(4-hydroxyphenyl)-5-(4-pyridyl) 1H-imidazole), SB 203580 (4-(4-fluorophenyl)-2-(4-methylsulfinylphenyl)-5-(4-pyridyl) 1H-imidazole), and U0126 (1,4-diamino-2,3-dycyano-1,4-bis(2-aminophenylthio) butadiene).

Preferably, the MAP kinase inhibitor is a p38 MAP kinase inhibitor. Examples of p38 MAP kinase inhibitors include (RS)-{4-[5-(4-Fluorophenyl)-2-methylsulfanyl-3H-imidazol-4-yl]pyridin-2-yl}-(1-phenylethyl)amine]; 2-(4-chlorophenyl)-4-(4-fluorphenyl)-5-pyridin-4-yl-1,2-dihydropyrazol-3-one; 4-(3-(4-chlorophenyl)-5-(1-methylpiperidin-4-yl)-1H-pyrazol-4-yl)pyrimidine; and N-(2-methoxy-4-thiomethyl)benzoyl-4-benzylpiperidine.

One embodiment of the invention provides a method of preparing a therapeutic composition comprising antigen-specific T cells or dendritic cells loaded with an antigen, the method comprising: (1) culturing antigen-specific T cells ex vivo in IL-15 in an amount and for a time effective to reduce Treg activity of the antigen-specific T cells; or (2) stimulating antigen-specific T cells ex vivo with antigen-loaded dendritic cells that are cultured ex vivo in IL-15 in an amount and for a time effective to reduce Treg activity of the antigen-specific T cells; or (3) culturing antigen-loaded dendritic cells ex vivo in a combination of IL-15 and a MAP kinase inhibitor in amounts and for a time effective to reduce Treg activity specific for the antigen in T cells contacted with the dendritic cells and to reduce Foxp3 expression in T cells contacted with the dendritic cells.

In one embodiment, the method comprises (2) stimulating antigen-specific T cells ex vivo with antigen-loaded dendritic cells that are cultured ex vivo in a combination of IL-15 and a MAP kinase inhibitor in amounts and for a time effective to reduce Treg activity of the antigen-specific T cells and to reduce Foxp3 expression in the antigen-specific T cells.

One embodiment of the invention provides a method of inhibiting Treg activity in response to a vaccine, the method comprising administering IL-15 to a mammalian subject (preferably a human patient) sequentially or concurrently with a vaccine containing an antigen to induce an immune response in the subject to the antigen, wherein the IL-15 is administered in an amount effective to inhibit Treg activity specific for the antigen.

Preferably, the vaccine comprises dendritic cells loaded with an antigen and prepared by culturing the dendritic cells ex vivo in IL-15 in an amount and for a time effective to inhibit Treg activity specific for the antigen.

In one embodiment, the dendritic cells are cultured in IL-15 before maturation and during maturation. "Maturation" is defined herein as the culture of dendritic cells in maturation cytokines, for example $PGE_2$, TNF$\alpha$, and IL-1$\beta$.

Preferably the IL-15 is administered to the mammalian subject in an amount and for a time effective to inhibit both CD4+ Treg activity and CD8+ T reg activity. But in some embodiments, it may inhibit only one or the other.

Preferably, the dendritic cells are cultured in IL-15 in an amount and for a time effective to inhibit CD4+ Treg activity and CD8+ Treg activity specific for the antigen (as compared to dendritic cells not cultured in IL-15) when the dendritic cells are used to activate T cells. But in some embodiments, only CD4+ or only CD8+ Treg activity may be inhibited.

The use of IL-15 is shown here to reduce Treg activity. Treg cells can also be selectively depleted. Two methods that may be used to achieve this are treatment of a mammalian subject or human patient with denileukin diftitox (7) or with cyclophosphamide (36-39). Thus, one embodiment of the methods of the invention involves depleting innate or tumor-associated regulatory T cells of the mammalian subject in association with administering a vaccine or composition of the invention. Preferably the step of depleting innate or tumor-associated regulatory T cells is prior to the step of administering IL-15 to the mammalian subject or prior to the step of administering a vaccine or therapeutic compositionto the subject.

In particular embodiments of the invention, the composition is to treat cancer and the antigen is a cancer antigen.

In specific embodiments, the cancer antigen is a matriptase antigen.

In other embodiments, the cancer antigen is an antigen of a protein selected from the group consisting of matriptase, hepsin, stratum corneum chymotryptic enzyme (SCCE), and CA125. The amino acid sequence of CA125 and information about CA125 antigens are disclosed in WO02083866 and WO04045553. The sequences and antigen information of matriptase, hepsin, and SCCE are disclosed in U.S. provisional patent application Ser. No. 60/860,714, filed Nov. 22, 2006. Each of those three documents are incorporated by reference.

Another embodiment of the invention provides a dendritic cell vaccine comprising: dendritic cells loaded with an antigen and cultured ex vivo in IL-15 in an amount and for a time effective to reduce Treg activity specific for the antigen in T cells contacted with the dendritic cells in a mammalian subject; and interleukin-15 in an amount effective to reduce Treg activity specific for the antigen in a mammalian subject.

In specific embodiments, the vaccine comprises IL-15 in an amount effective to reduce CD4+ Treg and CD8+ Treg responses in a mammalian subject specific to the antigen.

In specific embodiments, the vaccine is to treat cancer and the antigen is a cancer antigen, e.g., an antigen of matriptase, hepsin, SCCE, or CA125.

In specific embodiments, the dendritic cells are cultured in IL-15 before maturation and during maturation.

The invention will now be illustrated with the following Example, which is intended to illustrate the invention but not limit the embodiments thereof.

EXAMPLE 1

Interleukin-15 Enhances CD4+ and CD8+ Effector T Cell Function and Diminishes Regulatory T Cell Activity Induced by Cytokine-Matured Dendritic Cells

Materials and Methods

Cell Lines and Antibodies

EBV-transformed lymphoblastoid cell lines (LCL) were established from healthy adult donors as described (24). LCL were grown in RPMI 1640 medium supplemented with 10% FCS, $5\times10^{-5}$ M β-mercaptoethanol, 3 mM L-glutamine, 100 IU/ml penicillin and 100 μg/ml streptomycin (RPMI/10). DC were grown in AIM-V medium (Invitrogen, Carlsbad, Calif.). T cells were grown in RPMI supplemented with 10% human AB serum (Valley Biomedical, Winchester, Va.), $5\times10^{-5}$ M β-mercaptoethanol, 3 mM L-glutamine, 100 IU/ml penicillin and 100 μg/ml streptomycin (RPMI/10 Hu). Fluorochrome-conjugated anti-CD4 and anti-CD8 MAb were from Invitrogen. Foxp3-specific MAb and isotype control were from eBioscience (San Diego, Calif.). Fluorochrome-conjugated mAb specific for IL-4, IFNγ, IL-13 and TNFα were from BD Biosciences (San Jose, Calif.). MAb specific for glucocorticoid-induced TNF-receptor related gene product (GITR) was from R & D Systems (Minneapolis, Minn.). Cytokines for the establishment of DC and T cell cultures included GM-CSF (Immunex, Seattle, Wash.), IL-4, TNFα: and IL-15 (all from R & D Systems), $PGE_2$ (Sigma, St. Louis, Mo.), IL-1β and IL-2 (both provided by the Biological Response Modifiers Program, National Cancer Institute).

Peptides

Matriptase peptide 170-204 (ERVMAEERVV MLPPRARSLK SFVVTSVVAF PTDSK, SEQ ID NO:1) was synthesized by Alpha Diagnostic International (San Antonio, Tex.), to at least 95% purity, as determined by high-performance liquid chromatography. This peptide was selected from a computer analysis based on the algorithms of Southwood and colleagues for estimation of sequence binding affinities to HLA DR1, DR4 and DR7 (25). Collectively, HLA DR1, DR4 and DR7 molecules are expressed by 68.3% of Caucasians and an average of 48.8% of all ethnic groups overall. Available data suggest that a large set of DR molecules contain overlapping peptide binding repertoires, such that combined analysis of the DR1, DR4 and DR7 motifs has a high probability (>85%) of predicting degenerate HLA DR-binding epitopes, or multiple DR-binding clusters (25).

DC and T Cell Culture

Peripheral blood was drawn from healthy adult volunteer donors, following an IRB-approved protocol. PBMC were recovered by gradient centrifugation (Lymphoprep; Greiner Bio-One, Longwood, Fla.). For preparation of DC, PBMC were placed in 6 well plates (Costar, Cambridge, Mass.) at a concentration of $5\times10^6$/well in AIM-V medium. After incubation for 2-3 hours at 37° C., non-adherent cells were removed and the medium was replaced with AIM-V plus 800 U/ml GM-CSF and 500 U/ml IL-4. On days 3 and 5, half the medium was removed and replaced with AIM-V plus 800 U/ml GM-CSF and 500 U/ml IL-4. Maturation cytokines (1 μM/ml $PGE_2$, 1000 U/ml TNFα, and 500 U/ml IL-1β) were added on day 5. Where indicated, IL-15 (100 ng/ml) was present throughout DC culture (i.e., from day 0, and supplemented on days 3 and 5). For stimulation of peptide-specific $CD4^+$ helper T cell and $CD8^+$ CTL responses, DC were loaded with 50 μg/ml of peptide on day 5 (at the time of addition of maturation cytokines) and the DC were harvested 2 days later. The DC were then washed once with AIM-V medium and used for T cell stimulation at a PBMC:DC ratio of 30:1. After 7 days, T cells were collected and restimulated with peptide-loaded DC. After the second stimulation, $CD4^+$ or $CD8^+$ T cells were recovered by positive selection with anti-CD4 or anti-CD8 magnetic beads (Dynabeads, Invitrogen), respectively, yielding populations of at least 95% purity. During the second and subsequent T cell passages (up to a maximum of six restimulations with peptide-loaded DC, at T cell:DC ratios of between 30:1 and 10:1), 20-100 U/ml IL-2 was added to the medium, and the cultures were periodically fed (every 2-3 days) by changing 50-70% of the medium and addition of fresh IL-2. Where indicated, T cell cultures were supplemented with 100 ng/ml IL-15, starting with the second passage.

Intracellular Cytokine and Foxp3 Assays

Foxp3 expression was determined according to the manufacturer's staining protocol (eBioscience), using the provided fixation and permeabilization buffers. Intracellular cytokine expression was measured by flow cytometry after overnight co-culture of T cells with peptide-pulsed or control autologous LCL. T cells ($1.5\times10^6$) were plated in 12 well Costar plates in 2 ml RPMI/10Hu. T cells were stimulated with phorbol myristyl acetate (50 ng/ml) and ionomycin (500 ng/ml) as a positive control. At the onset of co-culture, 10 μg/ml of Brefeldin A was added to block cytokine release. Cells were collected after overnight stimulation and fixed in 2% paraformaldehyde in PBS for 10 minutes at room temperature. The cells were washed once in PBS and again in 0.5% saponin and 1% BSA in PBS. T cells were labeled with cytokine-specific PE or FITC-conjugated mAb for 30 minutes at room temperature. After staining, the cells were washed twice in 0.5% saponin and 1% BSA in PBS, once with 0.5% BSA in PBS, and fixed in 2% paraformaldehyde in PBS. Samples were analyzed with a FACSCalibur (Becton-Dickinson) and Cellquest or WinMDI software.

Cytotoxicity Assays

Standard $^{51}$Cr-release assays were performed as described (24). Autologous LCL were pulsed with 50 μg/ml peptide, or left unpulsed, in AIM-V medium overnight at 37° C. Peptide pulsed-targets were then labeled with 50 μCi $Na_2[^{51}Cr]O_4$ for one additional hour and washed three times before use. Target cells were plated at $1\times10^4$/well in 96-well round-bottomed plates with effector T cells at the ratios indicated for each assay. Assays were performed in triplicate wells. The percentage of target cell lysis was calculated as described (24).

Treg Assays

DC-activated, peptide-specific T cells were tested for Treg activity in 3 day microwell cocultures with autologous alloreactive $CD4^+$ T cells at a 1:1 ratio. The alloreactive $CD4^+$ T cells were stimulated with irradiated (7,500 cGy) allogeneic LCL at a 2:1 ratio. Transwell cocultures were conducted in 12-well Costar plates with 0.4 μm polycarbonate membrane inserts, at the same cell ratios as conventional microwell cocultures. Peptide-specific T cells were placed in the upper chamber, and alloreactive $CD4^+$ T cells plus irradiated allogeneic LCL were placed in the lower chamber. For all assays, proliferation of alloreactive $CD4^+$ T cells was determined by addition of 1 μCi/well $^3$H-TdR for the last 16 hours of incubation. No exogenous cytokines were added to Treg coculture assays. Controls were included to correct for background proliferation of individual cell populations or spontaneous alloreactivity of peptide-specific T cells.

Results

DC-Activated Matriptase Peptide-Specific $CD4^+$ T Cells Possess Treg Activity

Prior studies from our laboratory have shown that cytokine-matured DC loaded with extended peptides from serine protease antigens overexpressed by ovarian tumor cells activate effector T cell responses characterized by $CD4^+$ Th1 cytokine production and $CD8^+$ CTL responses (26). However, recent evidence has indicated that cytokine-matured DC not only activate effector T cell responses, but also efficiently activate and expand $CD4^+$ $Foxp3^+$ Treg (9). These observations prompted us to determine whether peptide-specific $CD4^+$ T cells activated with cytokine-matured DC also possessed Treg activity. We found that $CD4^+$ T cells specific for matriptase peptide 170-204 profoundly inhibited the proliferation of autologous alloreactive $CD4^+$ T cells in coculture assays (FIG. 1A). Treg activity was not confined to specificity for matriptase 170-204, or unique to this donor, since similar activity was seen with mature DC-activated $CD4^+$ T cells with other antigen specificities and from other individuals (not shown). Transwell assays, in which peptide-specific $CD4^+$ T cells were physically separated from the alloreactive $CD4^+$ T cells by a 0.4 μm permeable polycarbonate membrane, showed that Treg activity was at least in part mediated by soluble factors, as significant suppression of proliferation in the MLR was observed (FIG. 1B). However, Treg activity in the transwell coculture was less profound than in the contact coculture. This difference may indicate a co-dependence on cell contact for optimal Treg activity, or may reflect a relative inefficiency of cytokine-dependent Treg activity over distance. A further possibility is that DC expand heterogeneous Treg populations with differing modes of action, some of which may be dependent on cell-cell contact, and others operative through secretion of immunosuppressive cytokines, e.g., IL-10 and TGFβ1.

Does IL-15 Modulate the Treg Phenotype of Peptide-Specific DC-Activated T Cells?

Figure 2:
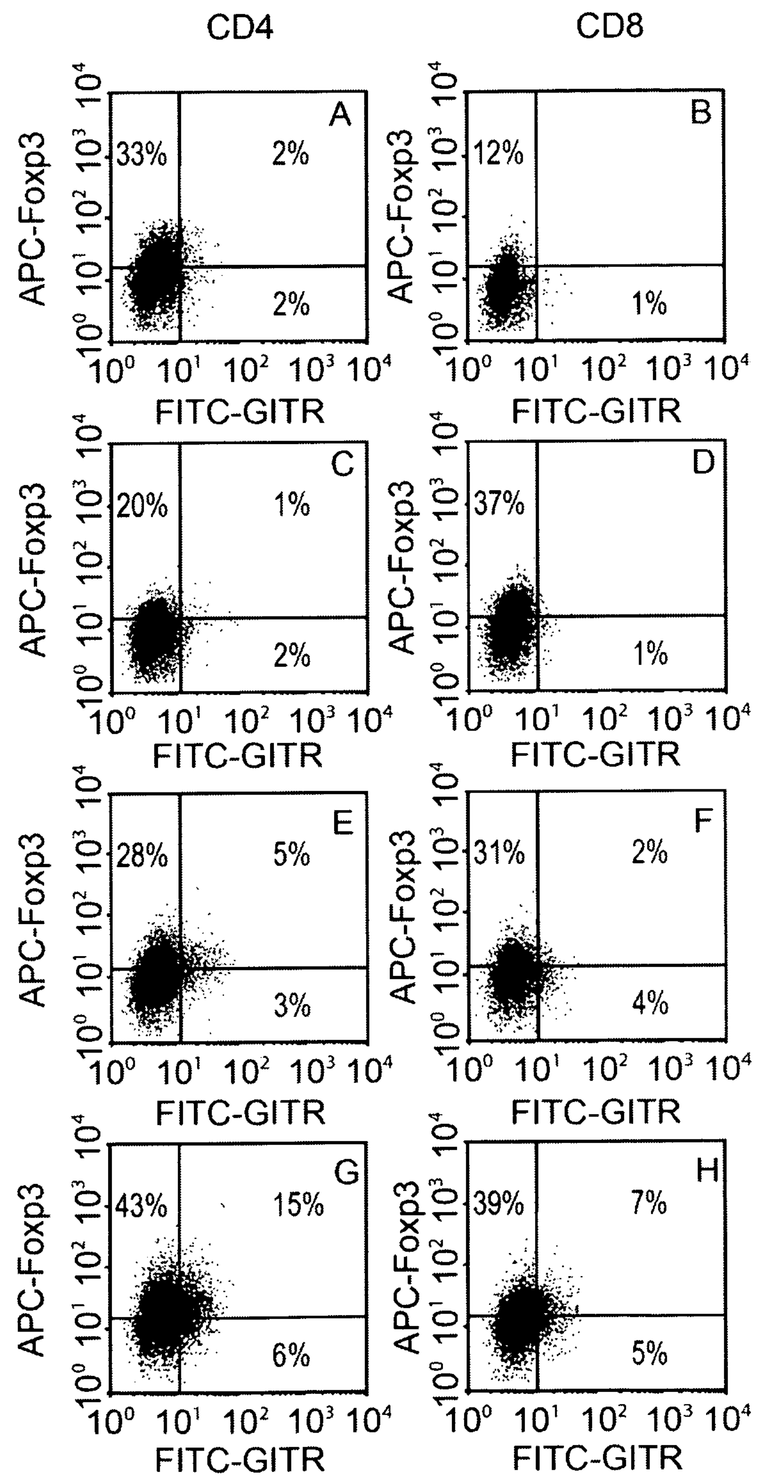
FIG. 2. Foxp3 and GITR expression by $CD4^+$ and $CD8^+$ T cells specific for matriptase peptide 170-204. T cell cultures were activated with conventional peptide-loaded DC and maintained with IL-2 (A, B), activated with IL-15 treated DC and maintained with IL-2 (C, D), activated with conventional DC and maintained with IL-2 plus IL-15 (E, F), or activated with IL-15 treated DC and maintained with IL-2 plus IL-15 (G, H).

In support of the functional evidence for Treg activity, flow cytometric analysis revealed that a significant proportion (33%) of matriptase 170-204 peptide-specific, DC-activated $CD4^+$ T cells expressed Foxp3 (FIG. 2A). In addition, a smaller proportion of $CD8^+$ T cells expressed a low level of Foxp3 (FIG. 2B). However, GITR was not expressed to a significant extent by $CD4^+$ or $CD8^+$ T cells (FIG. 2A-B). CD25 was broadly expressed by both $CD4^+$ and $CD8^+$ T cells (not shown), but since CD25 expression is activation-induced, it cannot be regarded as a reliable indicator of a Treg phenotype in this setting. However, expression of Foxp3 confirms that at least a subset of peptide-specific $CD4^+$ T cells possess regulatory function.

To determine whether IL-15 could modulate Foxp3 expression, we compared the phenotype of $CD4^+$ and $CD8^+$ T cells activated with conventional DC (cultured with GM-CSF and IL-4, followed by maturation with IL-1β, TNFα and $PGE_2$) and DC cultured with IL-15 in addition to the standard cytokines. $CD4^+$ T cells activated with IL-15-treated DC showed diminished Foxp3 expression (20%) relative to conventionally activated $CD4^+$ T cells (FIG. 2C), but $CD8^+$ T cells activated with IL-15-treated DC showed a marked increase in Foxp3 expression (37%) relative to conventionally activated $CD8^+$ T cells (FIG. 2D). Addition of IL-15 to $CD4^+$ T cell cultures activated with conventional DC did not result in a significant change in Foxp3 expression, but a small increase (total 8%) in the frequency of $GITR^+$ $CD4^+$ T cells was observed (FIG. 2E). A combination of activation with IL-15 treated DC and maintenance of T cells with IL-2 plus IL-15 markedly enhanced the frequency of both $Foxp3^+$ and $GITR^+$ $CD4^+$ T cells (FIG. 2G). Activation of $CD8^+$ T cells with conventional DC or IL-15-treated DC, in each case combined with maintenance of T cells with IL-2 plus IL-15, resulted in elevated frequencies of $Foxp3^+CD8^+$ T cells (FIGS. 2F and 2H), but did not show increased GITR expression. Collectively, phenotypic analysis shows that combined treatment of both DC and $CD4^+$ T cells with IL-15 induces increased expression of Treg phenotypic markers, suggesting that IL-15 may potentiate, rather than inhibit Treg function. In the case of $CD8^+$ T cells, treatment of either DC or T cells with IL-15 markedly increased Foxp3 expression, again suggesting Treg function may be enhanced.

IL-15 Antagonism of Treg Function

To determine whether increased expression of Foxp3 and GITR in response to IL-15 treatment of DC and/or T cells correlated with increased Treg activity, peptide-specific $CD4^+$ and $CD8^+$ T cells activated with conventional or IL-15-treated DC and maintained with IL-2 or IL-2 plus IL-15 were tested for regulatory function in cocultures with autologous alloreactive $CD4^+$ T cells. We found that IL-15 treatment of DC or T cells markedly diminished Treg activity (FIG. 3). Activation of peptide-specific $CD4^+$ T cells with IL-15-treated DC, or IL-15 treatment of $CD4^+$ T cells activated with conventional DC both resulted in significant restoration of the mixed lymphocyte reaction (MLR), with further enhancement of alloreactivity when both DC and $CD4^+$ T cells were treated with IL-15 (FIG. 3, upper panel). Irradiation of the peptide-specific $CD4^+$ T cells prior to coculture diminished regulatory function, and allowed almost total restoration of the MLR in cocultures with peptide-specific $CD4^+$ T cells activated with IL-15 treated DC, or activated with conventional DC and maintained with IL-2 plus IL-15, or activated with IL-15 treated DC and maintained with IL-2 plus IL-15 (FIG. 3, middle panel). These results indicate that IL-15 can inhibit Treg activity through two distinct mechanisms, either through direct action on $CD4^+$ T cells, or through an indirect pathway involving modification of DC function.

Peptide-specific $CD8^+$ T cells activated with conventional cytokine-matured DC also possessed strong regulatory function that was markedly diminished by IL-15 treatment of DC or IL-15 treatment of the $CD8^+$ T cells, or a combination of both treatments (FIG. 3, lower panel). IL-15 treatment of DC alone was particularly effective in diminishing $CD8^+$ Treg activity, with no significant enhancement observed from the combined treatment of both DC and peptide-specific $CD8^+$ T cells.

IL-15 Enhancement of $CD4^+$ Th1 Cytokine Expression

Figure 4:
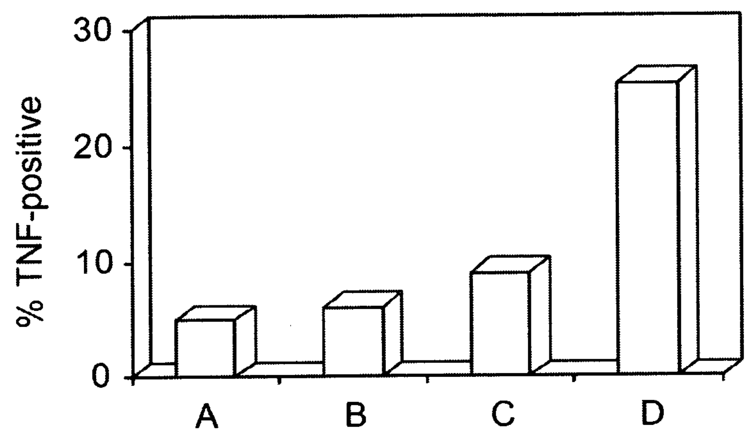
FIG. 4. IL-15 enhancement of antigen-specific $CD4^+$ T cell TNFα and IFNγ expression. Results are the means of three independent experiments, presented as percentage intracellular TNFα-expressing (upper panel) and IFNγ-expressing (lower panel) $CD4^+$ T cells following overnight activation with matriptase 170-204 peptide-loaded autologous LCL. The percentage of cytokine-expressing $CD4^+$ T cells in response to coculture with control autologous LCL (usually <2%) are subtracted from the data presented. Four conditions were tested: peptide-specific $CD4^+$ T cells activated with conventional DC and maintained with IL-2 (A), $CD4^+$ T cells activated with IL-15 treated DC and maintained with IL-2 (B), $CD4^+$ T cells activated with conventional DC and maintained with IL-2 plus IL-15 (C), or $CD4^+$ T cells activated with IL-15 treated DC and maintained with IL-2 plus IL-15 (D).
Figure 4:
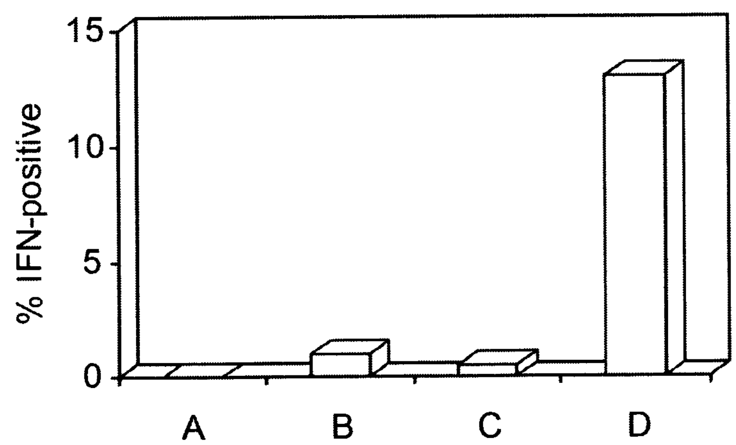

Since IL-15 treatment of DC or T cells markedly reduced Treg function, we determined whether the loss of Treg activity was matched by enhanced tumor antigen-specific $CD4^+$ effector function. Following the same combination of IL-15 treatments described above, we tested for $CD4^+$ T cell expression of TNFα and IFNγ, both of which are Th1 cytokines. A low frequency of conventional DC-activated $CD4^+$ T cells expressed TNFα upon challenge with peptide-loaded autologous LCL, and the IFNγ response was almost undetectable (FIG. 4). Treatment of DC with IL-15 or treatment of $CD4^+$ T cells with IL-15 resulted in a small increment in the frequency of T cells expressing TNFα and IFNγ, but combined IL-15 treatment of both DC and $CD4^+$ T cells resulted in a synergistic gain in antigen-driven cytokine responses (FIG. 4).

IL-15 Enhancement of Cytotoxic T Cell Function

Figure 5:
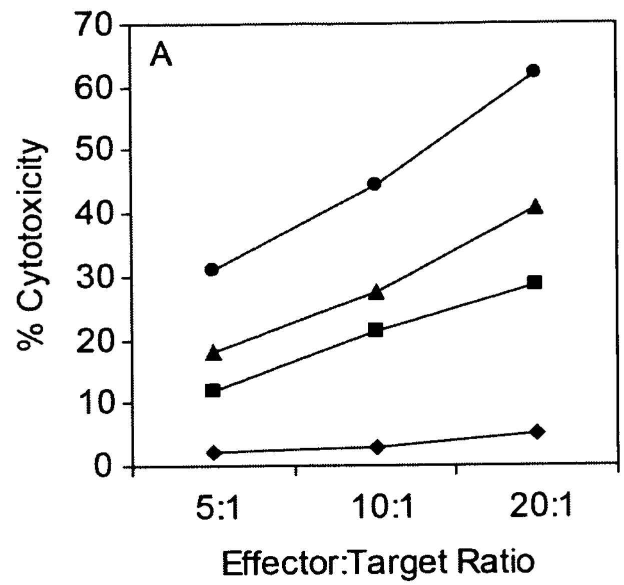
FIG. 5. IL-15 enhancement of peptide-specific cytotoxic T cell responses. Matriptase 170-204 peptide-specific $CD4^+$ T cells (A) and $CD8^+$ T cell (B) responses were tested in a standard 5-hour $^{51}$Cr-release assay against peptide-loaded autologous LCL. Four conditions were tested: peptide-specific T cells activated with conventional DC and maintained with IL-2 (♦), T cells activated with IL-15-treated DC and maintained with IL-2 (■), $CD4^+$ T cells activated with conventional DC and maintained with IL-2 plus IL-15 (▲), or $CD4^+$ T cells activated with IL-15-treated DC and maintained with IL-2 plus IL-15 (●). Control autologous LCL were not lysed by T cells derived from any of the conditions tested (not shown).
Figure 5:
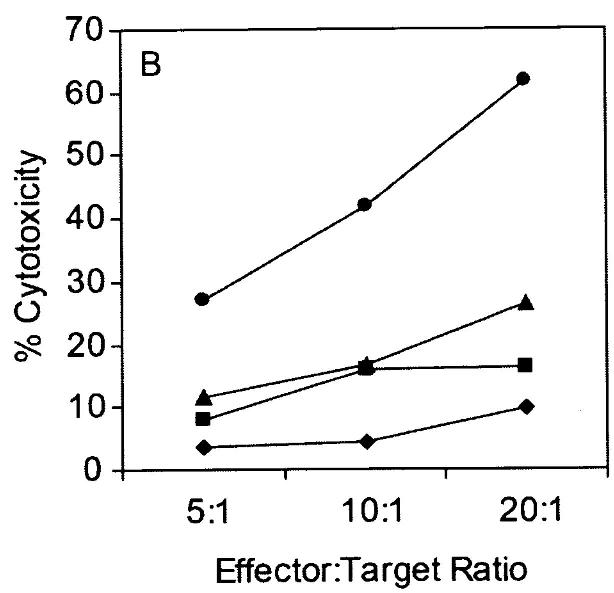

As noted above, $CD4^+$ T cell activation with IL-15-treated DC or T cell culture with IL-15 following activation with conventional DC had a minimal impact on Th1 cytokine responses. In contrast, IL-15 treatment of DC or $CD4^+$ T cells produced a marked enhancement of $CD4^+$ T cell cytoxicity in assays against peptide-loaded autologous LCL (FIG. 5A). The combination of $CD4^+$ T cell activation with peptide-loaded IL-15-treated DC followed by culture with IL-2 plus IL-15 resulted in a further gain in lysis of peptide-loaded LCL, the increase being additive rather than synergistic (FIG. 5A). Similar results were observed for $CD8^+$ T cell cytotoxicity against peptide-loaded LCL, except that the gain in lysis from IL-15 treatment of DC or $CD8^+$ T cells was lower than observed for $CD4^+$ T cell responses (FIG. 5B). However, combined treatment of both DC and $CD8^+$ T cells with IL-15 produced a strong synergistic increase in cytoxicity against peptide-loaded LCL (FIG. 5B). For both $CD4^+$ and $CD8^+$ T cell assays, minimal lysis was observed against control LCL, regardless of prior culture conditions (not shown).

Discussion

In agreement with the clinical observation that vaccination with cytokine-matured DC expands $CD4^+$ foxp3$^+$ Treg in myeloma patients (9), we found that tumor antigen-loaded DC matured with a standard cytokine cocktail (TNFα, IL-1β and $PGE_2$) activate and expand self antigen-specific $CD4^+$ foxp3$^+$ Treg in vitro. Our results do not distinguish between DC-driven expansion of innate, thymus-derived $CD4^+$ Foxp3$^+$ (and possibly $CD8^+$) Treg, and de novo recruitment of Treg from Foxp3$^-$ T cells. The innate Treg repertoire is likely to be heavily skewed towards recognition of self antigens by high avidity CD4 T cells (27), and thus DC may expand thymus-derived self-reactive Treg that recognize tumor antigens such as matriptase, but the possibility that cytokine-matured DC may drive Treg differentiation from non-regulatory T cell populations cannot be excluded. Although prior depletion of innate or tumor-associated Treg may result in enhanced immune responses and clinical benefit following DC vaccination (7), available evidence suggests that DC-driven activation and expansion of self-reactive Treg may nevertheless compromise anti-tumor effector T cell responses. For DC vaccination to be clinically effective, the new challenge is to identify alternative pathways of DC differentiation that bias T cell responses away from Treg homeostatis and in favor of active anti-tumor immunity.

Our initial phenotypic characterization of matriptase peptide-specific T cells expanded with cytokine-matured DC indicated that culture of T cells with IL-2 plus IL-15 expanded Foxp3$^+$ populations, particularly for the $CD8^+$ subset. IL-15-treated DC also increased the frequency of $CD8^+$ Foxp3$^+$T cells, relative to $CD8^+$ T cell cultures activated with conventional DC. Rather than supporting our hypothesis that IL-15 would diminish Treg activation, these observations apparently agreed with other studies suggesting that IL-15 could drive Treg growth and expansion (28, 29). However, analysis of Treg function in co-culture assays with autologous alloreactive $CD4^+$ T cells clearly showed that treatment of DC or T cell cultures with IL-15, and particularly combined treatment of both DC and T cells with IL-15, resulted in a striking abrogation of both $CD4^+$ and $CD8^+$ Treg activity. These observations suggest that Foxp3 expression may be intrinsic to T cells activated in the presence of IL-15, and cannot be interpreted as predictive of Treg function. Other recent studies have also indicated that Foxp3 expression is not limited to human Treg (31, 32).

The IL-15-driven abrogation of Treg function was mirrored by a significant increase in the frequency of antigen-responsive Th1 cytokine expressing $CD4^+$ T cells, most notably from combined treatment of both DC and T cell cultures with IL-15, which produced synergistic gains in the frequencies of $CD4^+$ T cells expressing TNFα and IFNβ. IL-15 treatment of DC or T cells also yielded marked improvements in $CD4^+$ and $CD8^+$ cytotoxic T cell responses, with a strong synergistic gain in $CD8^+$ CTL function resulting from combined IL-15 treatment of DC and T cells. It has previously been reported that IL-15-treated DC showed increased expression of E-cadherin, CCR6 and Langerin, all of which are markers for Langerhans cells (20), and thus the ability of IL-15-treated DC to diminish Treg activity and enhance T cell effector function may be related to redirection of differentiation towards a Langerhans phenotype. However, we did not observe increased expression of E-cadherin, CCR6 or Langerin following IL-15 treatment (not shown). This discrepancy may be attributed to differences in DC culture techniques; Mohamadzeh and colleagues added IL-15 but withdrew IL-4 from monocyte-derived DC cultures (20), whereas we maintained DC cultures in the presence of IL-15 and IL-4 throughout.

Although IL-15 is widely known for its ability to promote $CD8^+$ T cell memory and support $CD8^+$ T cell effector function, its ability to diminish both $CD8^+$ and $CD4^+$ Treg activity and enhance $CD4^+$ effector T cell responses are novel findings. IL-15 is not stimulatory per se for $CD4^+$ T cells, but IL-15 promotes the survival and supports the proliferation of activated $CD4^+$ T cells (33), which can express the high affinity IL-15Rα (34). However, expression of IL-15Rα by $CD4^+$ T cells is not a requirement for IL-15 to exert agonist activity, since IL-15 bound by other IL-15Rα-expressing cells (notably antigen-presenting cells, e.g., DC) may be trans-presented to $CD4^+$ T cells bearing the shared intermediate affinity IL-2/IL-15Rβ and γ chains, in similar fashion to its mode of action on $CD8^+$ T cells (35).

Collectively, these observations provide strong support for the incorporation of IL-15 into strategies for DC vaccination. We found that IL-15 treatment of DC markedly diminished expansion of $CD4^+$ and $CD8^+$ Treg, but IL-15-treated DC were not markedly more effective than conventional cytokine-matured DC in stimulating effector T cell responses (with the possible exception of $CD4^+$ CTL function). However, treatment of T cells with IL-15, particularly in combination with T cell activation by IL-15-treated DC, resulted in dramatic gains in both $CD4^+$ and $CD8^+$ effector function. From these observations, optimal anti-tumor immunity may be achieved by vaccination with IL-15-treated DC and co-administration of recombinant IL-15. An alternative and clinically more attractive approach that merits pursuit is the combination of IL-15-treated DC vaccination with prior depletion of innate or tumor-associated Treg, for example with denileukin diftitox (7) or cyclophosphamide (36-39), both of which are FDA-approved drugs.

EXAMPLE 2

Treatment of Dendritic Cells with IL-15 and a p38 MAP Kinase Inhibitor Enhances CD4⁺ Helper T Cell Function in T Cells Stimulated with the Dendritic Cells Materials and Methods Materials and Methods are as described in Example 1, except that the tumor antigen is hepsin peptide 48-84 (QEPLYPVQVSSADARLMVFDKTEGTWRLLCSSRSNAR (SEQ ID NO:2)), a serine protease widely expressed in epithelial cancers, notably ovarian cancer and prostate cancer.

Results

Figure 1:
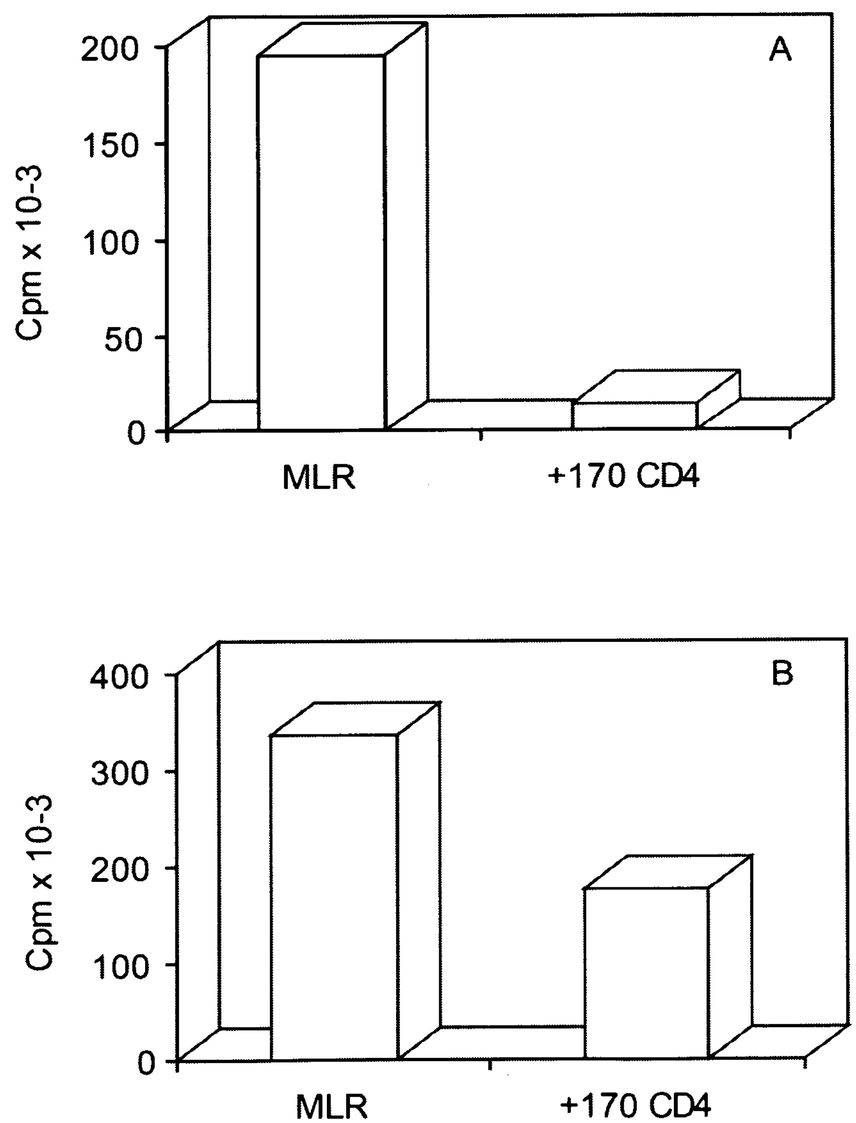
FIG. 1. Treg activity of DC-activated $CD4^+$ T cells specific for matriptase peptide 170-204. Peptide-specific $CD4^+$ T cells were activated with conventional DC and tested for Treg activity in 3 day cocultures with autologous alloreactive $CD4^+$ T cells at a 1:1 ratio. The alloreactive $CD4^+$ T cells were stimulated with allogeneic irradiated LCL at a 2:1 ratio. The assay was conducted in conventional contact cocultures (A) and in transwell cocultures in which the peptide-specific $CD4^+$ T cells were physically separated from the alloreactive $CD4^+$ T cells by a 0.4 μm polycarbonate membrane insert in a 12-well Costar plate (B). $^3$H-TdR was added for the final 16 hours of culture. Results are presented as the mean counts of 4 replicate cultures for the one-way MLR alone, or in coculture with DC-activated peptide-specific $CD4^+$ T cells.

Treatment of DC with IL-15 and a p38 MAP kinase inhibitor enhances $CD4^+$ helper T cell TNFα expression in response to tumor antigen stimulation, and diminishes Treg foxp3 expression. DC were treated with IL-15 (100 ng/ml) and/or a p38 MAP kinase inhibitor (10 μM p38 MAP kinase inhibitor III, from Calbiochem, La Jolla, Calif.) throughout their culture (i.e., from day 0 through completion of DC maturation on day 7). DC were loaded with the hepsin 48-84 peptide antigen on day 5 (i.e., at the time of addition of maturation cytokines). In this description, the combined treatment of DC with IL-15 and a p38 MAP kinase inhibitor markedly enhanced $CD4^+$ T cell TNFα expression upon tumor antigen stimulation, whereas treatment of DC with IL-15 alone, or p38MAP kinase inhibitor alone did not significantly increase TNFα expression by $CD4^+$ T cells, relative to expression by $CD4^+$ T cells activated with standard DC (FIG. 1). In contrast, treatment of DC with the combination of IL-15 and a p38 MAP kinase inhibitor almost totally abolished expression of the Treg transcription factor Foxp3 by tumor antigen-specific $CD4^+$ T cells (FIG. 6).

Figure 7:
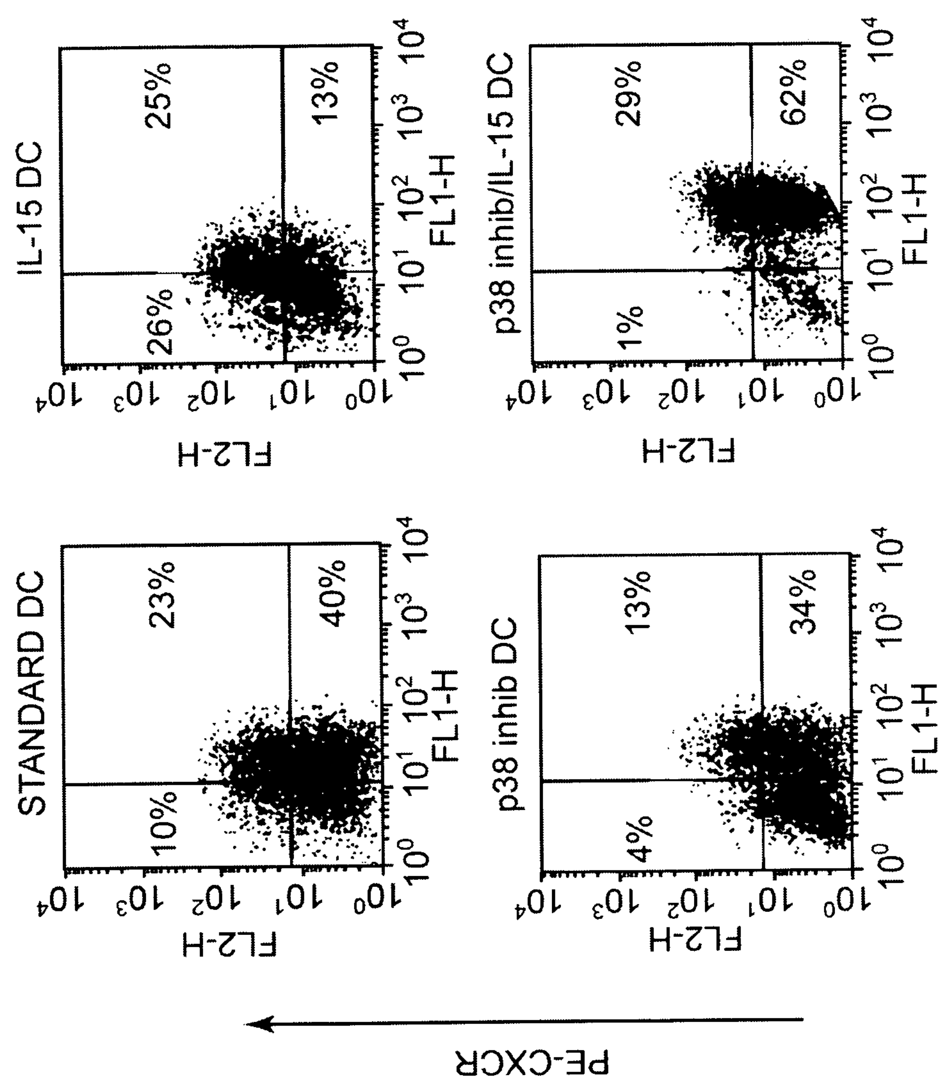
FIG. 7. CCR4 and CXCR4 expression by tumor antigen-specific CD4+ T cells stimulated with DC treated IL-15 and/or p38 MAP kinase inhibitor. Tumor antigen peptide-specific $CD4^+$ T cells were activated with conventional DC, IL-15-treated DC, DC treated with a p38 MAP Kinase inhibitor, or DC treated with both IL-15 and a p38 MAP kinase inhibitor. All $CD4^+$ T cell cultures were maintained with IL-2.

Treatment of DC with IL-15 and a p38 MAP kinase inhibitor modifies $CD4^+$ helper T cell expression of chemokine receptors CCR4 and CXCR4. IL-2 promotes Treg trafficking to tumors by inducing expression of CCR4 and CXCR4, which bind CCL22 and CXCL12 (stromal cell-derived factor-1, SDF-1), respectively (42, 43), both of which are abundantly produced in epithelial cancers, including ovarian tumors (42, 44). If Treg activation by DC can be inhibited, even in the presence of IL-2 (as shown by treatment of DC with IL-15 and p38 MAP kinase inhibitor in FIG. 1), but expression of CCR4 and CXCR4 is retained or enhanced, expression of these chemokine receptors may be harnessed to promote trafficking of anti-tumor $CD4^+$ helper T cells and $CD8^+$ cytotoxic T cells into the tumor microenvironment, thus affording greater therapeutic benefit following DC vaccination or adoptive T cell immunotherapy. We have found that IL-15 treatment of DC enhances $CD4^+$ T cell expression of CXCR4, but that CXCR4 expression is inhibited by treatment of DC with a p38 MAP kinase inhibitor (FIG. 7). In contrast, $CD4^+$ T cell expression of CCR4 is slightly inhibited by IL-15 treatment of DC, but markedly enhanced by the p38 MAP kinase inhibitor, and enhanced more by the combination of IL15 and the p38 MAP kinase inhibitor (FIG. 7). As CCL22 plays a major role in T cell trafficking in the tumor microenvironment, expression of its receptor, CCR4, is likely to boost infiltration of antitumor effector T cells.

Figure 8:
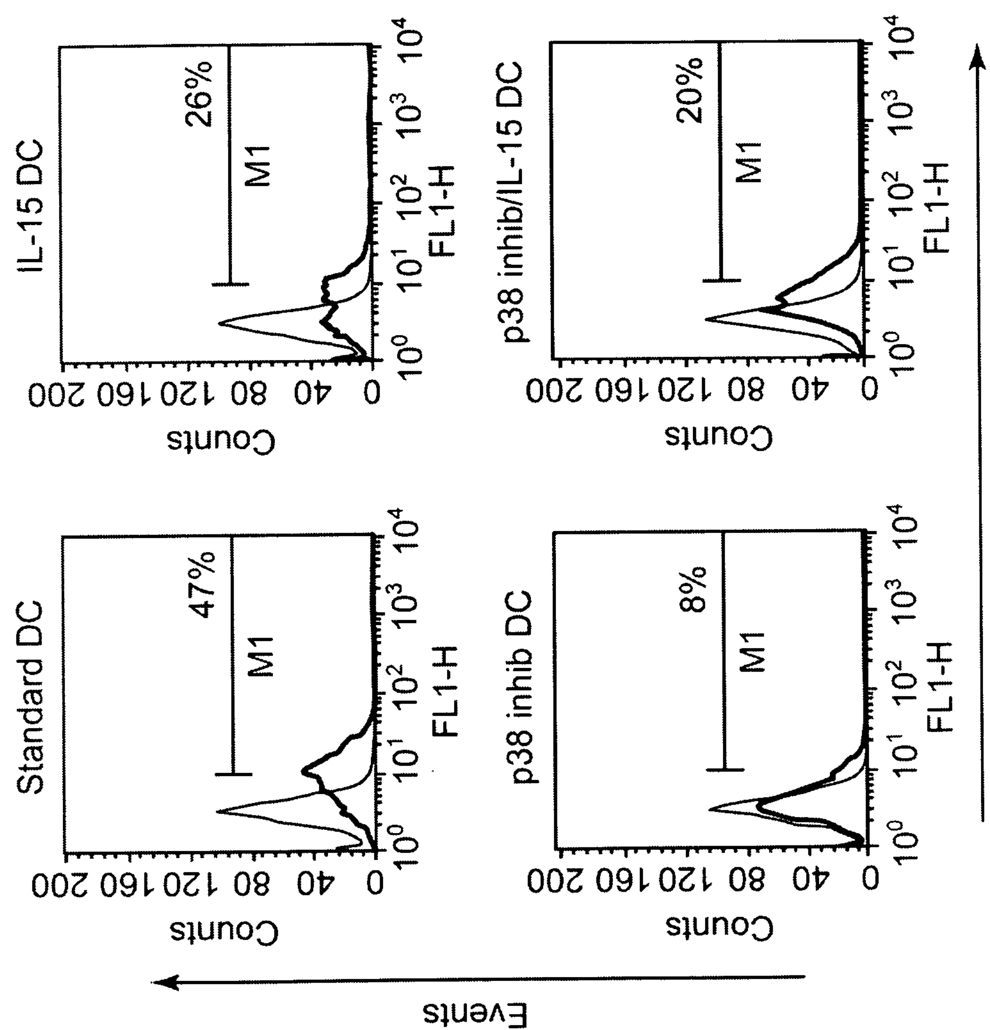
FIG. 8. PD-1 expression by tumor antigen-specific CD4+ T cells stimulated with DC treated IL-15 and/or p38 MAP kinase inhibitor. Tumor antigen peptide-specific $CD4^+$ T cells were activated with conventional DC, IL-15-treated DC, DC treated with a p38 MAP Kinase inhibitor, or DC treated with both IL-15 and a p38 MAP kinase inhibitor. All $CD4^+$ T cell cultures were maintained with IL-2.

Treatment of DC with IL-15 and a p38 MAP kinase inhibitor diminishes $CD4^+$ helper T cell expression of the inhibitory receptor PD-1. B7-H1 (PDL1, CD274) is expressed by many human cancers, including the majority of ovarian cancers, where it induces apoptosis of effector T cells and is thought to contribute to immune evasion (45). Increased expression of B7-H1 by tumor-associated myeloid DC also inhibits T cell responses, and blockade of B7-H1 improves DC-mediated antitumor immunity (46). The B7-H1 receptor on T cells is PD-1, which is readily expressed by tumor antigen-specific T cells following activation with conventional DC. We show that treatment of DC with IL-15, and particularly p38 MAP kinase inhibitor, markedly reduces PD-1 expression by tumor antigen-specific $CD4^+$ helper T cells (FIG. 8). In this instance, however, a synergistic benefit did not accrue from treatment of DC with both IL-15 and a p38 Map kinase inhibitor, i.e., the combined treatment did not further diminish $CD4^+$ T cell expression of PD-1. Collectively, these results indicate that anti-tumor effector T cells activated with DC treated with IL-15 or p38 MAP kinase inhibitor are likely to enjoy a survival advantage in the tumor microenvironment by virtue of diminished expression of PD-1.

Summary

We show that treatment of DC with IL-15 and a p38 MAP kinase inhibitor, and use of the DC to stimulate T cells increases $CD4^+$ T cell expression of CCR4, a receptor for the CCL22 chemokine that is responsible for trafficking of T cells into the tumor microenvironment. Finally, we show that treatment of DC with IL-15 and/or a p38 MAP kinase inhibitor diminishes $CD4^+$ T cell expression of the inhibitory receptor PD-1. The ligand for PD-1 is B7-H1, which is widely expressed in human tumors, and is responsible for induction of programmed cell death (apoptosis) of anti-tumor effector T cells. Diminished expression of PD-1 is thus likely to confer a survival advantage on tumor-infiltrating effector T cells.

REFERENCES

1. Gilboa E. DC-based cancer vaccines. J Clin Invest 2007; 117:1195-1203.
2. Curiel T J. Tregs and rethinking cancer immunotherapy. J Clin Invest 2007; 117:1167-74.
3. Knutson K L, Disis M L, Salazar L G. CD4 regulatory T cells in human cancer pathogenesis. Cancer Immunol Immunother 2007; 56:271-85.

4. Zou W. Regulatory T cells, tumour immunity and immunotherapy. Nature Rev Immunol 2006; 6:295-307.
5. Curiel T J, Coukos G, Zou L, et al. Specific recruitment of regulatory T cells in ovarian cancer fosters immune privilege and predicts reduced survival. Nature Med 2004; 10:942-9.
6. Wolf, D, Wolf A M, Rumpold H, et al. The expression of the regulatory T cell-specific forkhead box transcription factor FoxP3 is associated with poor prognosis in ovarian cancer. Clin Cancer Res 2005; 11:8326-31.
7. Dannull J, Su Z, Rizzieri D, et al. Enhancement of vaccine-mediated antitumor immunity in cancer patients after depletion of regulatory T cells. J Clin Invest 2005; 115: 3623-33.
8. Zhou G, Drake, CG, Levitsky H I. Amplification of tumor-specific regulatory T cells following therapeutic cancer vaccines. Blood 2006; 107:628-36.
9. Banerjee D K, Dhodapkar M V, Matayeva E, Steinman R M, Dhodapkar K M. Expansion of FOXP3high regulatory T cells by human dendritic cells (DCs) in vitro and after injection of cytokine-matured DCs in myeloma patients. Blood 2006; 108:2655-61.
10. Jonuleit H, Schmitt E, Schuler G, Knop J, Enk A H. Induction of interleukin 10-producing, nonproliferating $CD4^+$ T cells with regulatory properties by repetitive stimulation with allogeneic immature human dendritic cells. J Exp Med 2000; 192:1213-22.
11. Dhodapkar M V, Steinman R M, Krasovsky J, Munz C, Bhardwaj N. Antigen-specific inhibition of effector T cell function in humans after injection of immature dendritic cells. J Exp Med 2001; 193:233-8.
12. Dhodapkar M V, Steinman R M. Antigen-bearing immature dendritic cells induce peptide-specific $CD8^+$ regulatory T cells in vivo in humans. Blood 2002; 100:174-7.
13. Waldmann T A. Targeting the interleukin-15/interleukin-15 receptor system in inflammatory autoimmune diseases. Arth Res Ther 2004; 6:174-7.
14. Antony P A, Paulos C M, Ahmadzadeh M, et al. Interleukin-2-dependent mechanisms of tolerance and immunity in vivo. J Immunol 2006; 176:5255-66.
15. Rubinstein M P, Kadima A N, Salem M L, Nguyen C L, Gillanders W E, Cole D J. Systemic administration of IL-15 augments the antigen-specific primary $CD8^+$ T cell response following vaccination with peptide-pulsed dendritic cells. J Immunol 2002; 169:4928-35.
16. Klebanoff C A, Finkelstein S E, Surman D R, et al. IL-15 enhances the in vivo antitumor activity of tumor-reactive CD8+ T cells. Proc Natl Acad Sci USA 2004; 101:1969-74.
17. Roychowdhury S, May K F, Tzou K S, et al. Failed adoptive immunotherapy with tumor-specific T cells: reversal with low-dose interleukin 15 but not low-dose interleukin 2. Cancer Res 2004; 64:8062-7.
18. Teague R M, Sather B D, Sacks J A, et al. Interleukin-15 rescues tolerant $CD8^+$ T cells for use in adoptive immunotherapy of established tumors. Nature Med 2006; 12:335-41.
19. Dubois S P, Waldmann T A, Muller J R. Survival adjustment of mature dendritic cells by IL-15. Proc Natl Acad Sci USA 2005; 102:8662-7.
20. Mohamadzadeh M, Berard F, Essert G, et al. Interleukin 15 skews monocyte differentiation into dendritic cells with features of Langerhans cells. J Exp Med 2001; 194:1013-9.
21. Pulendran B, Dillon S, Joseph C, Curiel T, Banchereau J, Mohamadzadeh M. Dendritic cells generated in the presence of GM-CSF plus IL-15 prime potent $CD8^+$ Tc1 responses in vivo. Eur J Immunol 2004; 34:66-73.
22. Dubsky P, Saito H, Leogier M, et al. IL-15-induced human DC efficiently prime melanoma-specific naïve $CD8^+$ T cells to differentiate into CTL. Eur J Immunol 2007; 37:1678-90.
23. Tanimoto H, Underwood L J, Wang Y, Shigemasa K, Parmley T H, O'Brien T J. Ovarian tumor cells express a transmembrane serine protease: a potential candidate for early diagnosis and therapeutic intervention. Tumor Biol 2001; 22:104-14.
24. Nazaruk R A, Rochford R, Hobbs M V, Cannon M J. Functional diversity of the $CD8^+$ T cell response to Epstein-Barr virus: Implications for the pathogenesis of EBV-associated lymphoproliferative disorders. Blood 1998; 91:3875-83.
25. Southwood S, Sidney J, Kondo A, et al. Several common HLA-DR types share largely overlapping peptide binding repertoires. J Immunol 1998; 160:3363-73.
26. Bondurant K L, Crew M D, Santin A D, O'Brien T J, Cannon M J. Definition of an immunogenic region within the ovarian tumor antigen stratum corneum chymotryptic enzyme. Clin Cancer Res 2005; 11:3446-54.
27. Coutinho A, Caramalho I, Seixas E, Demengeot J. Thymic commitment of regulatory T cells is a pathway of TCR-dependent selection that isolates repertoires undergoing positive or negative selection. Curr Top Microbiol Immunol 2005:293; 43-71.
28. Bacchetta R, Sartirana C. Levings M K, Bordignon C, Narula S, Roncarolo M-G. Growth and expansion of human regulatory type 1 cells are independent from TCR activation but require exogenous cytokines. Eur J Immunol 2002; 32:2237-45.
29. Koenen HJPM, Fasse E, Joosten I. IL-15 and cognate antigen successfully expand de novo-induced human antigen-specific regulatory $CD4^+$ T cells that require antigen-specific activation for suppression. J Immunol 2003; 171: 6431-41.
30. Ahmadzadeh M, Antony P A, Rosenberg S A. IL-2 and IL-15 each mediate de novo induction of FOXP3 expression in human tumor antigen-specific CD8 T cells. J Immunother 2007; 30:294-302.
31. Morgan M E, van Bilsen J H M, Bakker A M, et al. Expression of FOXP3 mRNA is not confined to $CD4^+$ $CD25^+$ T regulatory cells in humans. Human Immunol 2005; 66:13-20.
32. Wang J, Ioan-Facsinay A, van der Voort E I, Huizinga T W, Toes R E. Transient expression of FOXP3 in human activated nonregulatory CD4+ T cells. Eur J Immunol 2007; 37:129-38.
33. Van Belle T, Grooten J. IL-15 and IL-15R□ in $CD4^+$ T cell immunity. Arch Immunol Ther Exp 2005; 53:115-26.
34. Chae D W, Nosaka Y, Strom T B, Maslinski W. Distirbution of IL-15 receptor alpha chains on human peripheral blood mononuclear cells and effect of immunosuppressive drugs on receptor expression. J Immunol 1996; 157:2813-19.
35. Waldmann T A. The biology of interleukin-2 and interleukin-15: implications for cancer therapy and vaccine design. Nature Rev Immunol 2006; 6:595-601.
36. Awwad M, North R J. Cyclophosphamide-induced immunologically mediated regression of a cyclophosphamide-resistant murine tumor: a consequence of eliminating precursor L3T4+ suppressor T-cells. Cancer Res 1989; 49:1649-54.
37. Bass K K, Mastrangelo M J. Immunopotentiation with low-dose cyclophosphamide in the active specific immunotherapy of cancer. Cancer Immunol Immunother 1998; 47:1-12.

38. Berd D, Sato T, Maguire Jr H C, Kairys J, Mastrangelo M J. Immunopharmacologic analysis of an autologous hapten-modified human melanoma vaccine. J Clin Oncol 2004; 22:403-15.

39. Lutsiak M E, Semnani R T, De Pascalis R, Kashmiri S V S, Schlom J, Sabzevari H. Inhibition of $CD4^{+}$ $CD25^{+}$ T regulatory cell function implicated in enhanced immune response by low-dose cyclophosphamide. Blood 2005; 105:2862-8.

40. Jarnicki A G, Conroy H, Brereton C, Donnelly G, Toomey D, Walsh K, Sweeney C, Leavy O, Fletcher J, Lavelle E C, Dunne P, Mills K H G. Attenuating regulatory T cell induction by TLR agonists through inhibition of p38 MAPK signaling in dendritic cells enhances their efficacy as vaccine adjuvants and cancer immunotherapeutics. J Immunol 180:3797-3806, 2008.

41. Wang S, Hong S, Yang J, Qian J, Zhang X, Shpall E, Kwak L W, Qing Y. Optimizing immunotherapy in multiple myeloma: resoring the function of patients' monocyte-derived dendritic cells by inhibiting p38 or activating MEK/ERK MAPK and neutralizing interleukin-6 in progenitor cells. Blood 108:4071-4077, 2008.

42. Curiel T J, Coukos G, Zou L, Alvarez X, Cheng P, Mottram P, Evdemon-Hogan M, Conejo-Garcia J R, Zhang L, Burow M, Zhu Y, Wei S, Kryczek I, Daniel B, Gordon A, Myers L, Lackner A, Disis M L, Knutson K, Chen L, Zou, W. Specific recruitment of regulatory T cells in ovarian cancer fosters immune privilege and predicts reduced survival. Nature Med 10:942-949, 2004.

43. Wei S, Kryczek I, Edwards R P, Zou L, Szeliga W, Banerjee M, Cost M, Cheng P, Chang A, Redman B, Herberman R B, Zou W. Interleukin-2 administration alters the $CD4^{+}$ $Foxp3^{+}$ T-cell pool and tumor trafficking in patients with ovarian carcinoma. Cancer Res 67:7487-7494, 2007.

44. Zou W, Machelon V, Coulomb-L'Hermin A, Borvak J, Nome F, Isaeva T, Wei S, Krzysiek R, Durand-Gasselin I, Gorodn A, Pustilnik T, Curiel D T, Galanaud P, Capron F, Emilie D, Curiel T J. Stromal-derived factor-1 in human tumors recruits and alters the function of plasmacytoid precursor dendritic cells. Nature Med 7:1339-1346, 2001.

45. Dong H, Strome S E, Salomao D R, Tamura H, Hirano F, Flies D B, Roche P C, Lu J, Zhu G, Tamada K, Lennon V A, Celis E, Chen L. Tumor-associated B7-H1 promotes T-cell apoptosis: a potential mechanism of immune evasion. Nature Med 8:793-800, 2002.

46. Curiel T J, Wei S, Dong H, Alvarez X, Cheng P, Mottram P, Krzysiek R, Knutson K L, Daniel B, Zimmermann M C, David O, Burow M, Gordon A, Dhurandhar N, Myers L, Berggren R, Hemminki A, Alvarez R D, Emilie D, Curiel D T, Chen L, Zou W. Blockade of B7-H1 improves myeloid dendritic cell-mediated antitumor immunity. Nature Med 9:562-567, 2003.

47. Qi M, Elion E A. MAP kinase pathways. J Cell Sci. 2005 Aug. 15; 118(Pt 16):3569-72.

48. Natarajan S R, Doherty J B. P38 MAP kinase inhibitors: evolution of imidazole-based and pyrido-pyrimidin-2-one lead classes. Curr Top Med Chem. 2005; 5(10):987-1003.

49. Dominguez C, Powers D A, Tamayo N. p38 MAP kinase inhibitors: many are made, but few are chosen. Curr Opin Drug Discov Devel. 2005 July; 8(4):421-30.

50. Avruch J. MAP kinase pathways: the first twenty years. Biochim Biophys Acta. 2007 August; 1773(8):1150-60.

51. Lee M R, Dominguez C. MAP kinase p38 inhibitors: clinical results and an intimate look at their interactions with p38alpha protein. Curr Med Chem. 2005; 12(25): 2979-94.

The patents, patent documents, and other references cited herein are incorporated by reference.

---

What is claimed is:

1. A method of preparing a therapeutic composition comprising antigen-specific T cells or dendritic cells loaded with an antigen, the method comprising:

(1) culturing adherent peripheral blood mononuclear cell (PBMC) dendritic cell recursors ex vivo in the presence of GM-CSF, IL-4, IL-15 and a p38 MAP kinase inhibitor in amounts and for a time effective to differentiate said precursors into dendritic cells that function to reduce Treg activity and FoxP3 expression in T cells, and further comprising stimulating antigen-specific T cells ex vivo with said dendritic cells that have been loaded with an antigen; or (2) culturing adherent PBMC dendritic cell precursors ex vivo in the presence of GM-CSF, IL-4, IL-15 and a p38 MAP kinase inhibitor in amounts and for a time effective to differentiate said precursors into dendritic cells that function to reduce Treg activity and Foxp3 expression in T cells contacted with the dendritic cells, and loading the dendritic cells with an antigen ex vivo.

2. The method of claim 1 wherein the method comprises:

(1) culturing adherent peripheral blood mononuclear cell (PBMC) dendritic cell recursors ex vivo in the presence of GM-CSF IL-4, IL-15 and a p38 MAP kinase inhibitor in amounts and for a time effective to differentiate said precursors into dendritic cells that function to reduce Treg activity and Foxp3 expression in T cells, and further comprising stimulating antigen-specific T cells ex vivo with said dendritic cells that have been loaded with an antigen.

3. The method of claim 2 wherein the method comprises (1) culturing adherent peripheral blood mononuclear cell (PBMC) dendritic cell recursors ex vivo in the presence of GM-CSF IL-4, IL-15 and a p38 MAP kinase inhibitor in amounts and for a time effective to differentiate said precursors into dendritic cells that function to reduce Treg activity and to reduce Foxp3 expression at least 2-fold in T cells, and further comprising stimulating antigen-specific T cells ex vivo with said dendritic cells that have been loaded with an antigen.

4. The method of claim 1 wherein the method comprises:

(2) culturing adherent PBMC dendritic cell precursors ex vivo in the presence of GM-CSF, IL-4, IL-15 and a p38 MAP kinase inhibitor in amounts and for a time effective to differentiate said precursors into dendritic cells that function to reduce Treg activity and Foxp3 expression in T cells contacted with the dendritic cells, and loading the dendritic cells with an antigen ex vivo.

5. A method of reducing Treg activity of T cells comprising:

(1) culturing adherent peripheral blood mononuclear cell (PBMC) dendritic cell precursors ex vivo in the presence of GM-CSF, IL-4, IL-15 and a p38 MAP kinase inhibitor in amounts and for a time effective to differentiate said precursors into dendritic cells that function to reduce Treg activity and FoxP3 expression in T cells, and further comprising stimulating antigen-specific T cells ex vivo with said dendritic cells that have been loaded with an antigen.

6. The method of claim 5 wherein the p38 MAP kinase inhibitor is (RS)-{4-[5-(4-fluorophenyl)-2-methylsulfanyl-3H-imidazol-4-yl]pyridin-2-yl}-(1-phenylethyl)amine]; 2-(4-chlorophenyl)-4-(4-fluorphenyl)-5-pyridin-4-yl-1,2-dihydropyrazol-3-one; 4-(3-(4-chlorophenyl)-5-(1-methylpiperidin-4-yl)-1H-pyrazol-4-yl)pyrimidine; or N-(2-methoxy-4-thiomethyl)benzoyl-4-benzylpiperidine.

* * * * *

SEQUENCE LISTING

```
<160> NUMBER OF SEQ ID NOS: 2

<210> SEQ ID NO 1
<211> LENGTH: 35
<212> TYPE: PRT
<213> ORGANISM: Homo sapiens

<400> SEQUENCE: 1

Glu Arg Val Met Ala Glu Glu Arg Val Val Met Leu Pro Pro Arg Ala
1               5                   10                  15

Arg Ser Leu Lys Ser Phe Val Val Thr Ser Val Val Ala Phe Pro Thr
            20                  25                  30

Asp Ser Lys
        35


<210> SEQ ID NO 2
<211> LENGTH: 37
<212> TYPE: PRT
<213> ORGANISM: Homo sapiens

<400> SEQUENCE: 2

Gln Glu Pro Leu Tyr Pro Val Gln Val Ser Ser Ala Asp Ala Arg Leu
1               5                   10                  15
```

-continued

```
Met Val Phe Asp Lys Thr Glu Gly Thr Trp Arg Leu Leu Cys Ser Ser
            20                  25                  30

Arg Ser Asn Ala Arg
        35
```